United States Patent [19]

Baacke et al.

[11] Patent Number: 4,563,480

[45] Date of Patent: Jan. 7, 1986

[54] CATALYST FOR THE PRODUCTION OF HYDROCARBONS AND PROCESS FOR THEIR PRODUCTION

[76] Inventors: Michael Baacke, Grunaustrasse 19, 6450 Hanau 9; Klaüs Deller, Friedhofstrasse 47, 6452 Hainburg; Peter Kleinschmit, Wildaustrasse 19, 6450 Hanau 9; Edgar Koberstein, Wolfskernstrasse 8, 8755 Alzenau, all of Fed. Rep. of Germany

[21] Appl. No.: 621,460

[22] Filed: Jun. 18, 1984

Related U.S. Application Data

[62] Division of Ser. No. 518,403, Jul. 29, 1983.

[30] Foreign Application Priority Data

Jul. 29, 1982 [DE] Fed. Rep. of Germany ....... 3228270

[51] Int. Cl.$^4$ ............................................... C07C 1/04
[52] U.S. Cl. ..................... 518/728; 502/64; 502/77; 502/78; 502/79
[58] Field of Search .......................................... 518/728

[56] References Cited

U.S. PATENT DOCUMENTS 3,013,984 12/1961 Breck .
4,096,163 6/1978 Chang et al. .
4,180,516 12/1979 Chang et al. .
4,472,535 9/1984 Chang et al. ........................ 518/728

OTHER PUBLICATIONS

Rees, Proceedings of Fifth International Conference on Zeolites Jun. 1980, pp. 562–570.

*Primary Examiner*—Howard T. Mars
*Attorney, Agent, or Firm*—Cushman, Darby & Cushman

[57] ABSTRACT

A catalyst for the production of hydrocarbon consists essentially of crystalline aluminum silicate, at least one compound of the metal zinc and/or cadmium and additionally silica. The catalyst is produced by heating a crystalline aluminum silicate, in a given case partially or completely converted to the hydrogen form, with a zinc and/or cadmium compound and molding with a silica containing binder.

14 Claims, No Drawings

CATALYST FOR THE PRODUCTION OF HYDROCARBONS AND PROCESS FOR THEIR PRODUCTION

This is a division of application Ser. No. 518,403, filed July 29, 1983.

BACKGROUND OF THE INVENTION

The invention is directed to a catalyst for the production of hydrocarbons having a higher ethane selectivity from synthesis gas (a mixture of carbon monoxide and hydrogen).

An important chemical raw material for the chemical industry is ethylene, which is produced to a great extent by cracking petroleum derivatives. In view of the expense and scarcity of petroleum products, it is also known to convert synthesis gas to a hydrocarbon mixture having the highest possible content of ethane, which then is further processed to ethylene (see Chang U.S. Pat. No. 4,096,163. The entire disclosure of Chang is hereby incorporated by reference and relied upon including the U.S. patents mentioned therein).

The industrially desired product is ethylene. This is obtained from paraffin hydrocarbons having at least two carbon atoms by cracking, whereby the highest yield is obtained from ethane. For this reason, it is desired to carry out the transfer of synthesis gas into hydrocarbons in such manner that there is obtained the highest possible content of ethane in the product gas mixture. In view of the very large amounts which are reacted in industrial plants, a slight improvement of the selectivity or the space-time-yields already represents a significant industrial advance.

It is known to produce aliphatic hydrocarbons from synthesis gas (see Chang U.S. Pat. No. 4,096,163, col. 13, example 7). The catalyst employed thereby is a zinc exchanged ZSM-5/aluminum oxide-extrudate. The hydrocarbon gas mixture obtained contained in addition to methane, isobutane, and isopentane (36.4% ethane and 11.9% propane).

Since the yield of ethane of the known process does not have the desired selectivity, there is a need to develop a corresponding catalyst.

SUMMARY OF THE INVENTION

The object of the invention is a catalyst for the production of hydrocarbons having higher ethane selectivity, consisting of (or consisting essentially of) crystalline aluminum silicate at least one compound of the metals zinc and/or cadmium and also silica.

Of especial interest as crystalline aluminum silicate is a zeolite. The zeolite can be of the structure type faujasite, mordenite and/or Pentasil (e.g., ZSM-5 and ZSM-11. Pentasil is described by Doelle et al in Journal of Catalysis, Vol. 71, pages 27–40 (1981). The entire disclosure of the Doelle article is hereby incorporated by reference and relied upon.

In a further illustrative form of the invention, the zeolite can be employed in pretreated form. A preparation of this type,, for example, can be an ion exchange, an impregnation, or a mixture with another component, preferably a compound of the metal, zinc and/or cadmium.

As metal, there is preferably present zinc. The supplementary silica can be present in the catalyst of the invention in amounts of 5 to 30 weight %, preferably 10 to 20 weight %, particularly 15 weight %, based on the aluminum silicate in powder form employed.

The zinc (and/or cadmium) content (calculated as ZnO or CdO) of the catalyst can be 0.1 to 30 weight %, preferably 0.5 to 3 weight %.

In a specific illustrative form, the zeolite used as aluminum silicate can have the following x-ray diffraction diagram with the following characteristic interferences:

| d-value | Int. |
|---|---|
| 11.17 ± 0.1 | 52 |
| 10.05 ± 0.1 | 35 |
| 6.34 ± 0.1 | 5 |
| 4.98 ± 0.03 | 4 |
| 4.35 ± 0.03 | 18 |
| 4.27 ± 0.03 | 23 |
| 3.85 ± 0.03 | 100 |
| 3.74 ± 0.03 | 54 |
| 3.66 ± 0.03 | 22 |
| 3.34 ± 0.03 | 8 |
| 2.98 ± 0.02 | 12 |
| 2.49 ± 0.02 | 12 |
| 2.00 ± 0.02 | 8 |

This type of zeolite which is of the type Pentasil can be produced by reaction of a mixture of water, sodium aluminate, sodium hydroxide, precipitated silica, and

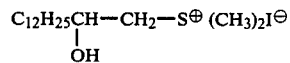

at a temperature of 50° to 200° C. under autogenous pressure in an autoclave and subsequent conversion into the hydrogen form.

The conversion into the hydrogen form can be carried by a known treatment with acids, preferably with mineral acids such as, e.g., sulfuric acid, hydrochloric acid, or nitric acid.

Likewise, the conversion into the hydrocarbon can be carried out by exchange with ammonium ions and subsequent calcination.

The conversion into the hydrogen form can be carried out completely or partially. In a preferred illustrative form, the $Na_2O$ content of the crystalline aluminum silicate converted into the hydrogen form can be less than 0.1 weight %.

The template compound

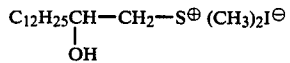

used can be produced as follows:

Tetradecene oxide (1) is reacted in known manner with methyl mercaptan to the sulfide (2) and this product is reacted with methyl iodide to form the end product (3).

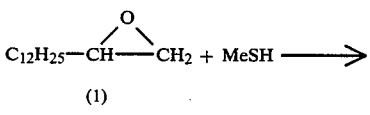

(1)

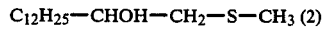

-continued

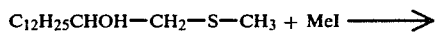

(2)

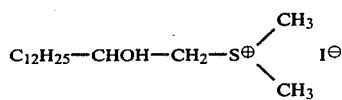

In a particular illustrative form, the catalyst of the invention can be present in shaped form, e.g., granulated, pelletized, extruded or tabletted.

In this form, the catalyst, if the pretreatment is carried out with a zinc compound, can have the following composition:
- 0.002 to 0.5 Wt.-% $Na_2O$
- 0.1 to 30 Wt.-% $ZnO$
- 0.4 to 5 Wt.-% $Al_2O_3$
- 60 to 98 Wt.-% $SiO_2$
- 2 to 15 Wt.-% Loss on calcining (DIN 51081)

For example, the composition can read as follows:
- 0.01 Wt.-% $Na_2O$
- 0.66 Wt.-% $ZnO$
- 1.39 Wt.-% $Al_2O_3$
- 91.51 Wt.-% $SiO_2$
- 5.4 Wt.-% Loss on calcining (DIN 51081)

Furthermore, the catalyst of the invention in shaped condition can have the following physical-chemical properties:
- (a) BET-Surface area 539 $m^2/g$
- (b) Hg-Compressed volume 0.99 $cm^3/g$
- (c) Sorption of n-Hexane 0.12 g/g, Benzene 0.06 g/g, 3-Methylpentane 0.09 g/g and water 0.06 g/g at $p/p_o = 0.5$ and $T = 23''c$ A further object of the invention is the process for production of the catalyst for the production of hydrocarbons with higher selectivity for ethane which are characterized by treating a crystalline aluminum silicate, preferably of the Pentasil type, in a given case either partially or completely converted into the hydrogen form, with a metal compound and molding with a silicon dioxide binder.

The treatment of the crystalline aluminum silicate, preferably Pentasil, with a metal compound can be carried out through ion exchange with a metal salt solution, impregnation with a metal sale solution, or mixing with solid metal oxide.

As metal compounds, there can be employed the oxides and/or the salts, as e.g., chloride, sulfate, nitrate, acetate, and others of zinc and/or cadmium.

The ion exchange can be carried out with an excess of zinc ions in aqueous solution in known manner. Thereby, there can be started with both the sodium form and also the hydrogen form of the crystalline aluminum silicate.

Since the sodium content of the catalyst preferably should be a low as possible, the impregnation (which term includes a drying) is carried out with aqueous zinc salt solution or the mixing with metal oxide preferably with a crystalline aluminum silicate of structural type Pentasil in the hydrogen form.

The amounts of metal compound added thereby corresponds to the final metal content of the crystalline aluminum silicate.

As silica containing binder, there can be employed in a preferred illustrative form silica sol or silica gel.

The molding of the crystalline aluminum silicate can take place according to known procedures.

For example, the molding can be carried out by addition of silica sol (40% silicon dioxide) to the aluminum silicate powder until reaching a moldable consistency and with subsequent shaping on a granulation plate. Likewise, a granulation is possible through, e.g., extrusion.

The catalyst of the invention can be employed for the production of hydrocarbons having higher ethane selectivity from synthesis gas (hydrogen and carbon monoxide).

As the gas employed, there are suited synthesis gas having varying amounts of hydrogen and carbon monoxide, as is known from the state of the art concerning the conversion of synthesis gas to hydrocarbons having a high ethane content. The synthesis gas without disadvantage can also contain smaller amounts of other gases such as carbon dioxide, methane, other lower hydrocarbons, e.g., propane, nitrogen, and gaseous sulfur compounds.

The molar ratio of hydrogen to carbon monoxide, suitably is in the range of 0.5:1 to 4:1, preferably in the range of 1:1 to 2:1. The possibility of using synthesis gas having this type of hydrocarbon is a special advantage of the catalysts of the invention since the synthesis gas can practically pass into the composition resulting from the carbon gasification without enrichment with hydrogen and without expensive gas purification.

The pressure used lies in the ranges that are known in the art, whereby in the selection of the operating pressure besides the purely reaction-kinetics factors there can also be considered the pressure of the synthesis gas available and/or the pressure desired for the product gas. As especially suited, there has proven a total-reaction pressure of 5 to 400 bar, preferably of 20 to 200 bar, and especially preferred below 150 bar.

The reaction temperature likewise can be varied within wide limits as in accordance with the state of the art, whereby a range of 300° to 550° C., and especially of 340° to 460° C. is preferred. It is an advantage of the process according to the invention that the conversion can be carried out at relatively high temperatures with excellent results.

The process according to the invention can be carried out with solid bed or fluidized bed catalyst. There can be employed the same reactors as are used according to the state of the art for conversion of synthesis gas. Examples of suitable reactors are those which are also employed for the methanol-synthesis, e.g., step reactors having cold gas addition, step reactors having intermediate cooling, tube reactors having internal or external cooling. The removal of heat is carried out according to the state of the art, e.g., by liquids or gases.

There can also be employed reactors such as are known for the Fischer-Tropsch synthesis; e.g., tube reactors, step reactors, fluidized bed reactors, or According to the process of the invention, a hydrocarbon mixture having a very high portion of ethane is obtained at good space-time-yields. Besides ethane, as is according to the state of the art, there are formed substantially methane, ethylene, propane, propylene, and isobutane.

The gas mixture obtained according to the invention can be used in various ways, e.g., by mixing with natural gas to increase the heating value. A specially important use industrially, however, is in the production of ethylene. For this purpose, the ethane and the higher hydrocarbons are separated according to known process from the hydrocarbon-gas mixture obtained, e.g., by pressure washing with mineral oils. The separated ethane and the higher hydrocarbons are converted into ethylene according to known processes in the art. (See Ullmann's Enzyklopädie. Tech. Chem. 4th Edition, Vol. 8, pages 158–194). The entire disclosure of Ullmann is hereby incorporated by reference and relied upon.

The catalyst can consist of or consist essentially of the stated materials; and the process can comprise, consist essentially of, or consist of the stated steps with the recited materials.

DETAILED DESCRIPTION
EXAMPLES
A. Production of the Catalyst
Example 1

5 grams of sodium aluminate and 25 grams of NaOH were dissolved in 50 ml of $H_2O$ and added to a suspension of 200 grams of precipitated silica and 75 grams of $C_{12}H_{25}CHOHCH_2-S^{\oplus}(CH_3)_2I^{\ominus}$ in 2000 ml of $H_2O$. The mixture was stirred for 80 hours at 160° C. in an autoclave under autogenous pressure, filtered off and washed to pH 9 with $H_2O$. The wet filter cake was suspended in 2 liters of ethyl alcohol, filtered off, washed with ethyl alcohol, and dried at 120° C. 100 grams of the dried silicate were stirred in 1 liter of 2 normal HCl for 2 hours at 80° C., filtered off, washed with water until neutral, and dried at 120° C.

Analysis: 0.06% $Na_2O$; 1.74% $Al_2O_3$; 91.1% $SiO_2$; 3.2% Loss on Calcining.

The aluminum silicate had an x-ray diffraction diagram (pattern) having the following characteristic interferences:

| d-Value | Int. |
| --- | --- |
| 11.17 ± 0.1 | 52 |
| 10.05 ± 0.1 | 35 |
| 6.34 ± 0.1 | 5 |
| 4.98 ± 0.03 | 4 |
| 4.35 ± 0.03 | 18 |
| 4.27 ± 0.03 | 23 |
| 3.85 ± 0.03 | 100 |
| 3.74 ± 0.03 | 54 |
| 3.66 ± 0.03 | 22 |
| 3.45 ± 0.03 | 7 |
| 3.34 ± 0.02 | 8 |
| 2.98 ± 0.02 | 12 |
| 2.49 ± 0.02 | 12 |
| 2.00 ± 0.02 | 8 |

Example 2

50 grams of aluminum silicate according to Example 1 were stirred in a solution of 136.3 grams of $ZnCl_2$ in 500 ml of $H_2O$ for one hour at 80° C., filtered off, washed with water, and dried. The zinc treated aluminum silicate obtained had the following composition:
0.01 Wt.-% $Na_2O$
1.63 Wt.-% $Al_2O_3$
92.5 Wt.-% $SiO_2$
0.74 Wt.-% ZnO

Example 3

50 grams of aluminum silicate according to Example 1 without acid treatment (0.75% $Na_2O$.1.52% $Al_2O_3$.89.6% $SiO_2$) were stirred into a solution of 500 grams of $ZnCl_2$ in 500 ml of water for two hours at 80° C. and subsequently worked up as described in Example 2.

The zinc treated aluminium silicate obtained had the following composition:
0.18 Wt.-% $Na_2O$
1.15 Wt.-% $Al_2O_3$
85.9 Wt.-% $SiO_2$
1.17 Wt.-% ZnO

Example 4

50 grams of aluminum silicate as described in Example 1 were suspended in a solution of 1.25 grams of $ZnCl_2$ in 100 ml of water and stirred for 2 hours at 80° C. The mixture obtained was dried at 50° C./50 mbar.

The zinc treated aluminum silicate obtained had the following composition:
0.03 Wt.-% $Na_2O$
1.54 Wt.-% $Al_2O_3$
89.7 Wt.-% $SiO_2$
1.5 Wt.-% ZnO

Example 5

50 grams of aluminum silicate according to Example 1 in the hydrogen form and 1.5 grams of ZnO were suspended in 100 ml of water and stirred for 2 hours at 80° C. The mixture obtained was dried at 50° C. and a pressure of 50 mbar.

The zinc salt pretreated silicate obtained had the following composition:
0.04 Wt.-% $Na_2O$
1.70 Wt.-% $Al_2O_3$
89.6 Wt.-% $SiO_2$
2.9 Wt.-% ZnO

Example 6

The aluminum silicate employed as in Example 4 was treated analogously with an aqueous zinc acetate solution. Under otherwise identical conditions, there were used 4.3 grams of zinc acetate. The zinc salt pretreated aluminum silicate obtained was subsequently calcined at 440° C. and had the following composition:
0.02 Wt.-% $Na_2O$
1.26 Wt.-% $Al_2O_3$
88.5 Wt.-% $SiO_2$
3.1 Wt.-% ZnO

Example 7

Shaping 50 grams of pretreated powdery aluminum silicate according to Examples 1 to 6 were mixed with 15 ml of 40% silica sol and 15 ml of water to form a pasty composition and shaped in the granulating plate. After the drying (4 hours at 120° C.), the granulates were calcined at 440° C. and sieved. The fraction 0.5 to 1 mm was used for the reaction of the synthesis gas.

B. Reaction of $CO/H_2$
Example 1

A synthesis gas mixture, which contains $H_2$ and CO in the molar ratio 2:1, was led over the catalyst bed at a temperature of 400° C., a pressure of 80 bar and a volume related space velocity of 500 $h^{-1}$.

The results obtained thereby are set forth in Table 1.

TABLE 1

Conversion of Synthesis Gas On Aluminum Silicate According To Example A 2 Which Was Shaped According to Example 7

| | |
|---|---|
| Temperature °C. | 400 |
| Pressure, bar | 80 |
| Space Velocity Volume/Volume h | 500 |
| Conversion of CO to Hydrocarbons % | 18 |
| $H_2$/CO in | 2 |
| Total Conversion of Synthesis Gas % | 25 |
| Distribution of Hydrocarbon Wt. % | |
| Methane | 22 |
| Ethane | 70 |
| Propane | 5 |
| $C_4^+$ | 3 |

Example 2

The conversion of the synthesis gas was carried out in a fixed bed reactor having a diameter of 10 mm and 60 ml of reaction space. There were filled into the reactor 40 ml of the catalyst obtained according to production Example A2. The catalyst was activated by leading nitrogen through it in an amount of 10 l/h at 450° C. under a pressure of 2 bars for 4 hours.

The synthesis gas was led through the reactor whereby composition, space velocity, reaction temperature, and reaction pressure are collected in following Table 2. In this table, there are given the total conversion of synthesis gas, the conversion of carbon monoxide to hydrocarbons and the distribution of the hydrocarbons.

The gas mixture leaving the reactor was relieved of pressure and led through a cooling trap at −20° C. No condensation product was deposited in the cooling trap. The gas mixture leaving the cooling trap was led through gas sample tubes for analysis.

TABLE 2

| | | | | |
|---|---|---|---|---|
| Synthesis gas, $H_2$:CO | 1.65 | 1.65 | 1.65 | 1.65 |
| Space Velocity Volume/Volume .h | 500 | 500 | 500 | 500 |
| Reaction Temperature, °C. | 350 | 350 | 350 | 350 |
| Reaction Pressure, bar | 80 | 200 | 300 | 400 |
| Total Converson of Synthesis Gas | 4 | 6 | 10 | 12. |
| Conversion of CO to Hydrocarbons, % | 4 | 7 | 9 | 11 |
| Distribution of Hydrocarbons Wt. % | | | | |
| Methane | 18.5 | 24.0 | 24.0 | 25.1 |
| Ethane | 50.0 | 42.1 | 37.0 | 30.6 |
| Propane | 4.5 | 8.0 | 9.9 | 10.2 |
| Butane and Higher | 27.0 | 25.9 | 29.0 | 34.0 |

Example 3

The procedure was as described in Example B2, whereby the process parameters and results are collected in the following Table 3.

TABLE 3

| | | | | | |
|---|---|---|---|---|---|
| Synthesis gas, $H_2$:CO | 1.62 | 1.62 | 1.62 | 1.62 | 1.62 |
| Space Velocity Volume/Volume .h | 500 | 500 | 500 | 500 | 500 |
| Reaction Temperature, °C. | 350 | 375 | 400 | 425 | 450 |
| Reaction Pressure, bar | 100 | 100 | 100 | 100 | 100 |
| Total Conversion of Synthesis Gas % | 6.6 | 8.8 | 14.5 | 19.9 | 22.5 |
| Conversion of CO to Hydrocarbons % | 5.8 | 6.5 | 12.5 | 18.2 | 20.3 |
| Distribution of Hydrocarbons Wt. % | | | | | |
| Methane | 27.3 | 29.8 | 29.6 | 30.0 | 50.2 |
| Ethane | 49.5 | 56.2 | 60.6 | 60.7 | 39.8 |
| Propane | 12.1 | 6.8 | 6.8 | 6.8 | 5.9 |
| Butane and Higher | 11.1 | 7.2 | 3.1 | 2.5 | 4.2 |

Example 4

The procedure was as described in Example B2, whereby the process parameters and results are collected in the following Table 4.

TABLE 4

| | | | |
|---|---|---|---|
| Synthesis Gas, $H_2$:CO | 1.18 | 1.65 | 3.0 |
| Space Velocity Volume/Volume .h | 500 | 500 | 500 |
| Reaction Temperature, °C. | 400 | 400 | 400 |
| Reaction Pressure, bar | 100 | 100 | 100 |
| Total Conversion of Synthesis Gas, % | 24.9 | 14.5 | 17.9 |
| Conversion of CO to Hydrocarbons, % | 20.1 | 12.5 | 16.0 |
| Distribution of Hydrocarbons Wt. % | | | |
| Methane | 37.5 | 29.6 | 48.0 |
| Ethane | 45.0 | 60.6 | 36.5 |
| Propane | 10.2 | 6.8 | 8.6 |
| Butane and Higher | 7.3 | 3.1 | 6.9 |

Example 5

The procedure was as described in Example B2, whereby the process parameters and results are collected in the following Table 5.

TABLE 5

| | | |
|---|---|---|
| Synthesis Gas, $H_2$:CO | 1.65 | 1.65 |
| Space Velocity Volume/Volume .h | 125 | 125 |
| Reaction Temperature, °C. | 400 | 425 |
| Reaction Pressure, bar | 100 | 100 |
| Total Conversion of Synthesis Gas, % | 29.6 | 40.1 |
| Conversion of CO to Hydrocarbons, % | 23.3 | 31.5 |
| Distribution of Hydrocarbons in Wt. % | | |
| Methane | 21.0 | 35.0 |
| Ethane | 69.9 | 55.0 |
| Propane | 5.0 | 6.1 |
| Butane and Higher | 4.1 | 3.9 |

Example 6

The reaction was as in Example B1.

TABLE 6

Reaction of Synthesis Gas On Aluminum Silicate According To Example A 6 Which Was Shaped According to Example 7

| | |
|---|---|
| Temperature °C. | 400 |
| Pressure Bar | 80 |
| Space Velocity Volume/Volume .h | 500 |
| $H_2$/CO in | 2.2 |
| Conversion of CO to Hydrocarbons | 17.4 |
| Total Conversion of Synthesis Gas | 18.0 |
| Distribution of Hydrocarbons Wt. % | |
| Methane | 29.0 |
| Ethane | 62.0 |
| Propane | 5.0 |

TABLE 6-continued

Reaction of Synthesis Gas On Aluminum Silicate According To Example A 6 Which Was Shaped According to Example 7

| | |
|---|---|
| $C_4^+$ | 4.0 |

Example 7

50 grams of commercial Zeolite Y was exchanged analogous to Example A2 and used for synthesis gas conversion.

TABLE 7

| | |
|---|---|
| Temperature °C. | 500 |
| Pressure bar | 80 |
| Space Velocity Volume/Volume .h | 500 |
| $H_2$/CO in | 2.2 |
| Conversion of CO to Hydrocarbons | 21.0 |
| Total Conversion of Synthesis Gas | 24.7 |
| Distribution of Hydrocarbons Wt. % | |
| Methane | 51 |
| Ethane | 41 |
| Propane | 6 |
| $C_4^+$ | 2 |

Example 8

50 grams of the commercial zeolite mordenite in the hydrogen form was impregnated according to Example A6 using 9 grams of zinc acetate and used for the synthesis gas reaction. The results are set forth in Table 8.

TABLE 8

7% ZnO/Mordenite
Pressure 100 bar $H_2$/CO in = 1.72

| | | | | After 20 h |
|---|---|---|---|---|
| Temperature °C. | 350 | 375 | 400 | 425 |
| Space Velocity | 650 | 650 | 650 | 650 |
| Contraction, % | ~2 | 4.5 | 7.5 | 10.3 |
| Conversion of CO to Hydrocarbons, % | ~3 | 7.5 | 11.2 | 14.2 |
| Conversion CO+$H_2$, % | ~3 | 8.0 | 13.4 | 18.5 |
| Out $H_2$/CO | ~1.8 | 1.85 | 1.0 | 1.05 |
| Out $CO_2$, Vol. % | 1.0 | 1.8 | 3.5 | 4.7 |
| Distribution of Hydrocarbons | | | | |
| $C_1$, Wt. % | 36.0 | 37.5 | 34.6 | 36.6 |
| $C_2$ | 39.1 | 45.7 | 53.5 | 56.2 |
| $C_3$ | 17.8 | 12.1 | 8.6 | 5.9 |
| $C_4$ | 7.0 | 3.6 | 2.4 | 0.9 |
| $C_5^+$ | 0.2 | 1.1 | 0.9 | 0.3 |

The entire disclosure of German priority application P 3228270.2 is hereby incorporated by reference.

What is claimed is:

1. In a process for the production of hydrocarbons from synthesis gas in the presence of a catalyst, the improvement comprising increasing the selectivity for forming ethane by employing as the catalyst a catalyst consisting essentially of (1) crystalline aluminum silicate, (2) at least one zinc or cadmium compound or a mixture of compounds of both zinc and cadmium, and (3) additional silica.

2. A process according to claim 1 wherein the catalyst contains 0.1 to 30% zinc or cadmium calculated as ZnO or CdO and containing 5 to 30% silica based on the amount of aluminum silicate.

3. A process according to claim 2 wherein the catalyst contains 0.1 to 30% zinc calculated as ZnO.

4. A process according to claim 3 wherein the catalyst contains 10 to 20% zinc calculated as ZnO and 0.5 to 3% silica based on the amount of aluminum silicate.

5. A process according to claim 1 wherein the crystalline aluminum silicate is a zeolite.

6. A process according to claim 5 wherein the zeolite is a pretreated zeolite.

7. A process according to claim 6 wherein the pretreatment is by ion exchange with a compound of zinc or cadmium.

8. A process according to claim 5 wherein the zeolite is faujasite, mordenite, or Pentasil.

9. A process according to claim 8 wherein the zeolite has an x-ray diffraction diagram as follows:

| d-Value | Int. |
|---|---|
| 11.17 ± 0.1 | 52 |
| 10.05 ± 0.1 | 35 |
| 6.34 ± 0.1 | 5 |
| 4.98 ± 0.03 | 4 |
| 4.35 ± 0.03 | 18 |
| 4.27 ± 0.03 | 23 |
| 3.85 ± 0.03 | 100 |
| 3.74 ± 0.03 | 54 |
| 3.66 ± 0.03 | 22 |
| 3.45 ± 0.03 | 7 |
| 3.34 ± 0.02 | 8 |
| 2.98 ± 0.02 | 12 |
| 2.49 ± 0.02 | 12 |
| 2.00 ± 0.02 | 8 |

10. A process according to claim 9 wherein the zeolite is one produced by reacting a mixture of water, sodium aluminate, precipitated silica, and

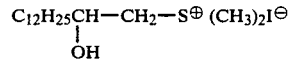

at a temperature of 50° to 200° C. under autogenous pressure in a closed container followed by conversion into the hydrogen form.

11. A process according to claim 8 wherein the zeolite is one produced by reacting a mixture of water, sodium aluminate, precipitated silica, and

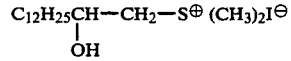

at a temperature of 50° to 200° C. under autogenous pressure in a closed container followed by conversion into the hydrogen form.

12. A process according to claim 1 wherein the synthesis gas has a molar ratio of hydrogen to carbon monoxide of 0.5:1 to 4:1, the pressure is 5 to 400 bar and the temperature is 300° to 550° C.

13. A process according to claim 12 wherein the molar ratio of hydrogen to carbon monoxide is 1:1 to 2:1, the pressure is 20 to 200 bar and the temperature is 340° to 460° C.

14. A process according to claim 1 wherein the catalyst consists of (1), (2), and (3).

* * * * *

UNITED STATES PATENT AND TRADEMARK OFFICE
CERTIFICATE OF CORRECTION

PATENT NO. : 4,563,480
DATED : January 7, 1986
INVENTOR(S) : BAACKE ET AL

It is certified that error appears in the above-identified patent and that said Letters Patent is hereby corrected as shown below:

IN THE COVER SHEET:

Item 30 should be added and should recite "German Patent 3228270, filed July 29, 1982".

Signed and Sealed this

Twelfth Day of August 1986

[SEAL]

Attest:

Attesting Officer

DONALD J. QUIGG

Commissioner of Patents and Trademarks